(12) United States Patent
Dahl

(10) Patent No.: US 10,259,718 B2
(45) Date of Patent: Apr. 16, 2019

(54) PROCESS FOR CO-PRODUCTION OF AMMONIA AND METHANOL

(71) Applicant: Haldor Topsøe A/S, Kgs. Lyngby (DK)

(72) Inventor: Per Juul Dahl, Vedbæk (DK)

(73) Assignee: HALDOR TOPSØE A/S, Kgs. Lyngby (DK)

(*) Notice: Subject to any disclaimer, the term of this patent is extended or adjusted under 35 U.S.C. 154(b) by 0 days.

(21) Appl. No.: 15/527,657

(22) PCT Filed: Dec. 2, 2015

(86) PCT No.: PCT/EP2015/078272
§ 371 (c)(1),
(2) Date: May 17, 2017

(87) PCT Pub. No.: WO2016/096410
PCT Pub. Date: Jun. 23, 2016

(65) Prior Publication Data
US 2017/0327383 A1    Nov. 16, 2017

(30) Foreign Application Priority Data

Dec. 15, 2014  (EP) .................................... 14197991

(51) Int. Cl.
*C01B 3/12*     (2006.01)
*C01C 1/04*    (2006.01)
(Continued)

(52) U.S. Cl.
CPC ........ *C01C 1/0488* (2013.01); *C07C 29/1518* (2013.01); *C07C 31/04* (2013.01);
(Continued)

(58) Field of Classification Search
CPC ... C01C 1/0488; C07C 31/04; C07C 29/1518; C07C 1/322; C07C 1/12; C07C 1/04; C01B 3/12; Y02P 20/52
See application file for complete search history.

(56) References Cited

U.S. PATENT DOCUMENTS 3,598,527 A    8/1971  Quartulli et al.
5,180,570 A    1/1993  Lee et al.
(Continued)

FOREIGN PATENT DOCUMENTS

WO    WO 2011/020618 A1    2/2011

OTHER PUBLICATIONS

International Search Report with Written Opinion corresponding to International Patent Application No. PCT/EP2015/078272, dated Feb. 8, 2016.
(Continued)

*Primary Examiner* — Anthony J Zimmer
(74) *Attorney, Agent, or Firm* — Leydig, Voit & Mayer, Ltd.

(57) ABSTRACT

In a process for co-production of ammonia and methanol, the outlet stream from the reformer is split into two parts, one of which is subjected to shift, carbon dioxide removal, methanation, compression and ammonia synthesis, while the other part is compressed and fed to a once-through methanol synthesis section. Methanol is withdrawn from the methanol synthesis section, and the remaining effluent from said section is divided into two streams comprising hydrogen, of which one is fed to the shift section, while the other is recycled to the desulfurization unit. This way a favourable co-production method is obtained because recycle hydrogen for the desulfurization is provided, and furthermore a compression step is avoided.

5 Claims, 1 Drawing Sheet

(51) Int. Cl.
*C07C 1/04* (2006.01)
*C07C 1/12* (2006.01)
*C07C 1/32* (2006.01)
*C07C 31/04* (2006.01)
*C07C 29/151* (2006.01)

(52) U.S. Cl.
CPC ............... *C01B 3/12* (2013.01); *C07C 1/04* (2013.01); *C07C 1/12* (2013.01); *C07C 1/322* (2013.01); *Y02P 20/52* (2015.11)

(56) References Cited

U.S. PATENT DOCUMENTS

| | | | |
|---|---|---|---|
| 6,333,014 B1 | 12/2001 | Filippi | |
| 2010/0150810 A1* | 6/2010 | Yoshida | B01J 8/0411 423/359 |
| 2012/0148472 A1* | 6/2012 | Ahmed | C01B 3/025 423/359 |

OTHER PUBLICATIONS

European Search Report corresponding to European Patent Application No. 14197991.4, dated Jun. 3, 2015.

\* cited by examiner

PROCESS FOR CO-PRODUCTION OF AMMONIA AND METHANOL

CROSS-REFERENCE TO RELATED APPLICATIONS

This application is a U.S. National Stage Application filed under 35 U.S.C § 371 of International Application No. PCT/EP2015/078272, filed Dec. 2, 2015, which claims the benefit of EP Application No. 14197991.4, filed Dec. 15, 2014. Both of these applications are hereby incorporated by reference in their entireties.

The present invention relates to a novel process for co-production of ammonia and methanol.

Figure 1:
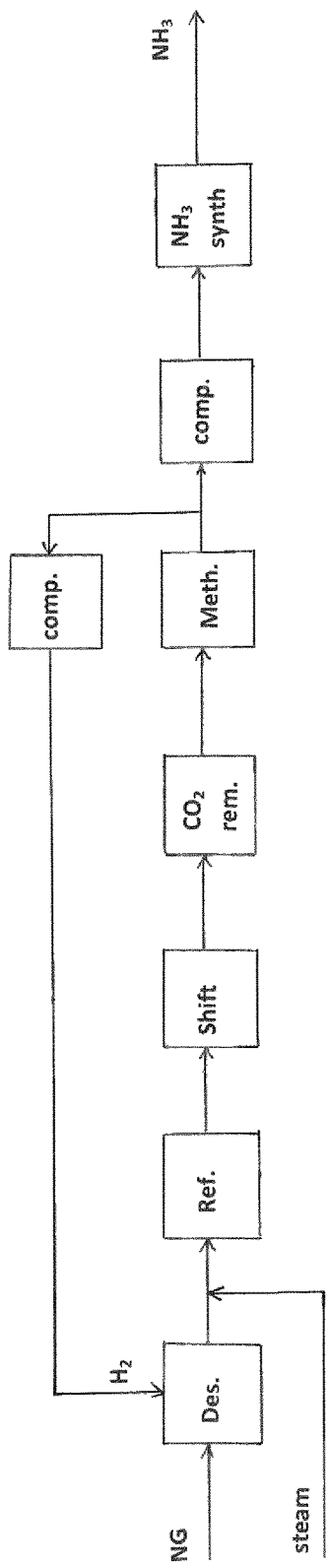
FIG. 1 shows the standard method comprising desulfurization (Des.) of a hydrocarbon feed, such as natural gas (NG) in the presence of compressed recycle hydrogen (comp.), addition of steam to the desulfurized natural gas followed by reforming (Ref.), shift, CO2 removal (CO2 rem.) and methanation (Meth.) of the process stream, recycle of a portion of the methanated stream to the desulfurization step (Des.) and compression (comp.) of the remaining portion of methanated steam followed by synthesis of ammonia (NH3 synth).

It is known that ammonia and methanol can be co-produced by a standard method as shown in FIG. 1, said standard method comprising the following steps:

desulfurization of a hydrocarbon feed gas in the presence of compressed recycle hydrogen,
addition of steam to the desulfurized natural gas followed by reforming, shift, $CO_2$ removal and methanation of the process stream,
recycle of a portion of the methanated stream to the desulfurization step, thereby providing compressed recycle hydrogen to this step, and
compression of the remaining portion of methanated steam followed by synthesis of ammonia.

The hydrocarbon feed is a mixture of steam and optionally pre-reformed hydrocarbons. These hydrocarbons may originate from any hydrocarbon sources that can be used for reformer feeding, such as natural gas.

Figure 2:
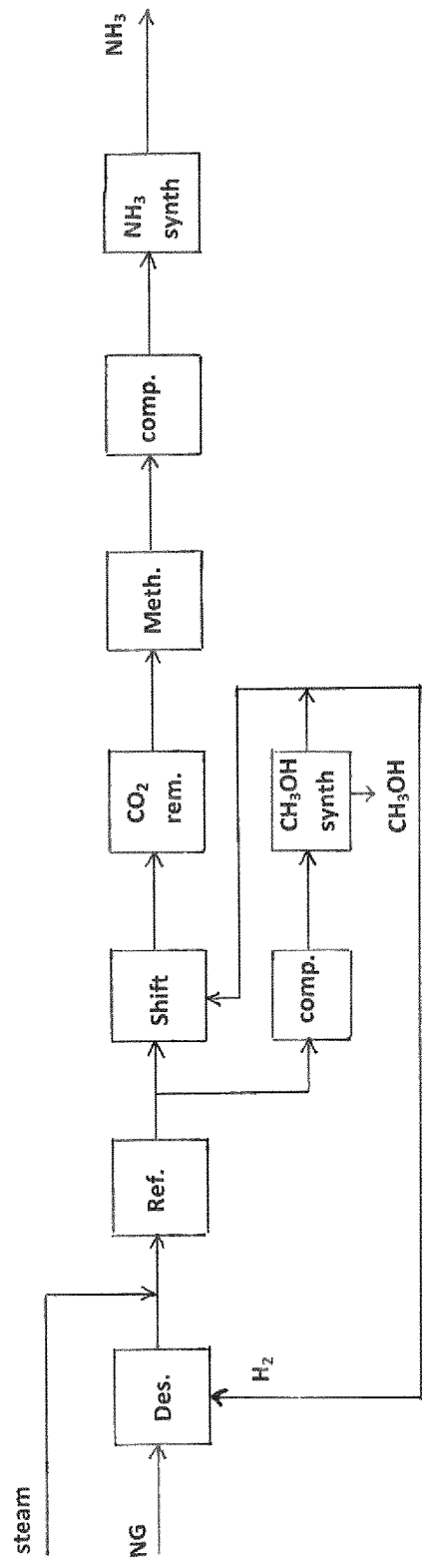
FIG. 2 shows the novel process of the invention for co-production of ammonia and methanol comprising desulfurization (Des.) of a hydrocarbon feed, such as natural gas (NG), in the presence of hydrogen, addition of steam to the desulfurized natural gas followed by reforming (Ref.), shift, carbon dioxide removal (CO2 rem.) and methanation (Meth.), where the outlet stream from the reformer is split into two parts, one of which is subjected to shift, carbon dioxide removal (CO2 rem.), methanation (Meth.), compression (comp.) and ammonia synthesis (NH3 synth), while the other part is compressed (comp.) and fed to a once-through methanol synthesis section (CH3OH synth), methanol (CH3OH) is withdrawn from the methanol synthesis section, and the remaining effluent from said section is divided into two streams comprising hydrogen, and one of the two streams comprising hydrogen is fed to the shift section, while the other stream comprising hydrogen is recycled to the desulfurization unit.

The novel process according to the present invention, shown in FIG. 2, covers the following modifications of the above standard method:

the recycle of a portion of the methanated stream to the desulfurization step is not carried out,
the reformed stream is split into two parts: (a) a first reformed stream that is subjected to shift, $CO_2$ removal and methanation according to the standard method, and (b) a second reformed stream that is compressed and used for methanol synthesis in a once-through methanol synthesis section comprising one to three reactors in series,
removal of a stream of gaseous components from the methanol synthesis section and division of this stream into two streams comprising hydrogen,
transfer of a first stream comprising hydrogen to the shift section, typically to a point between the high temperature shift and the low temperature shift, and
transfer of a second stream comprising hydrogen to the desulfurization step, thereby providing recycle hydrogen for the desulfurization and thus replacing the recycle hydrogen previously provided by the methanated stream in the standard process.

The crux of the present invention, compared to the standard process, is to utilize part of the syngas from the methanol synthesis as recycle hydrogen. That way, it is possible to save a dedicated recycle compressor. Similarly, for existing ammonia plants, where a small amount of methanol is requested, the compressor used to provide compressed recycle hydrogen to the desulfurization step can also be used as compressor for the methanol synthesis.

Integrated processes for co-production of ammonia and methanol are known in the art. Thus, WO 2011/020618 relates to a process for co-producing methanol and ammonia, wherein a syngas mixture consisting essentially of CO, $CO_2$ and $H_2$ is first partially reacted in a methanol once-through reactor, un-reacted syngas is divided into a first and a second stream, the first stream is purified and fed to an ammonia synthesis section, and the second stream is fed to a methanol synthesis and purification. This process enables high capacity production of methanol and ammonia in an integrated single process, applying unit operations not exceeding current practical capacity limitations.

An integrated process for co-producing methanol and ammonia is also disclosed in U.S. Pat. No. 6,333,014, which process comprises the steps of reforming desulfurized hydrocarbon with steam and air in a primary and a secondary reformer to make a syngas mixture, dividing the syngas mixture into a first and a second syngas stream, cooling the first syngas stream to remove a water stream and feeding remaining syngas to a methanol once-through reactor to make a methanol-containing mixture, separating the methanol-containing mixture into crude methanol and a methanol-free gas, feeding the second syngas stream to a high-temperature CO converter, feeding the effluent from the high-temperature CO converter, the methanol-free gas and the water stream to a low-temperature CO converter and feeding the effluent from the low-temperature CO converter to an ammonia synthesis section to make ammonia.

U.S. Pat. No. 5,180,570 discloses an integrated process for making methanol and ammonia similar to the present invention. It comprises two recycles: A first portion of unreacted methanol synthesis gas is recycled to the methanol synthesis reactor, and a second portion of unreacted methanol synthesis gas is withdrawn as a purge gas stream containing i.a. $H_2$ (70-90 mole %), CO (1-7 mole %) and $CO_2$ (1-7 mole %). The production of ammonia can be boosted when the CO component of the unreacted methanol synthesis gas purge stream is catalytically reacted with steam in a shift section. This is then followed by $CO_2$ removal, and the hydrogen content is thus further enhanced. Further processing includes wash, compression and ammonia synthesis; methanation is not mentioned. In the disclosed process, the needs for steam shift and methanation are obviated, unless a boost in ammonia production is required.

U.S. Pat. No. 3,598,527 discloses an ammonia and methanol production process which shows some similarity to the present invention. A portion of the methanol synthesis gas stream is passed to a low pressure water gas shift zone for conversion of CO to $CO_2$. Furthermore, purge gases from the methanol synthesis loop are fed to a high temperature shift. The process disclosed in the US patent utilizes a single process chain, whereby substantial savings in operation costs of carbon dioxide compression are obtained, and additional savings are obtained by using a single process chain instead of independent methanol and ammonia plants.

The above-identified prior art does not disclose a process in which only a second reformed stream is compressed and used in methanol synthesis. Furthermore, the prior art does not disclose the transfer of a second stream containing hydrogen to the desulfurization step, thereby providing recycle hydrogen for the desulfurization and also avoiding a compression step.

Thus, with reference to FIG. 2, the present invention concerns a novel process for co-production of ammonia and methanol comprising desulfurization (Des.) of a hydrocarbon feed, such as natural gas (NG), in the presence of hydrogen, addition of steam to the desulfurized natural gas followed by reforming (Ref.), shift, carbon dioxide removal ($CO_2$ rem.) and methanation (Meth.), wherein the outlet stream from the reformer is split into two parts, one of which is subjected to shift, carbon dioxide removal, methanation, compression (comp.) and ammonia synthesis ($NH_3$ synth), while the other part is compressed and fed to a once-through methanol synthesis section ($CH_3OH$ synth), methanol ($CH_3OH$) is withdrawn from the methanol synthesis section, and the remaining effluent from said section is divided into two streams comprising hydrogen, one of the two streams comprising hydrogen is fed to the shift section, and the other stream comprising hydrogen is recycled to the desulfurization unit.

The hydrocarbon feed is preferably natural gas, but it can be any mixture of steam and optionally pre-reformed hydrocarbons, where these hydrocarbons may originate from any hydrocarbon sources that can be used for reformer feeding. The part of the reformer outlet stream, which is compressed and fed to the methanol synthesis section, is preferably compressed to 40-100 bar, most preferably around 80 bar.

The methanol synthesis section comprises one methanol synthesis reactor or two or three such reactors connected in series.

The process of the invention is further illustrated by means of the following example.

EXAMPLE

A reformer outlet gas obtained by desulfurization of a hydrocarbon feed gas in the presence of hydrogen has the following composition (dry gas) in percent:

| Ar | 0.22 |
| $CH_4$ | 0.56 |
| CO | 12.76 |

-continued

| $CO_2$ | 7.81 |
| $H_2$ | 59.73 |
| $N_2$ | 18.92 |

The flow of this dry gas is 22996 $Nm^3/h$.

The gas is split into two streams, and one of these (43.5%) is passed through the methanol section, where it is compressed to a pressure above 80 bar and converted to 18950 kg/h methanol and 56763 $Nm^3/h$ of a hydrogen-rich gas with the following composition (dry gas) in percent:

| Ar | 0.38 |
| $CH_3OH$ | 0.05 |
| $CH_4$ | 0.97 |
| CO | 3.43 |
| $CO_2$ | 8.38 |
| $H_2$ | 53.58 |
| $N_2$ | 33.31 |

For the desulfurization of the hydrocarbon feed gas in the presence of hydrogen, 3275 $Nm^3/h$ of the dry hydrogen-rich gas with a pressure above 45 barg has to be recycled to the desulfurization section.

The ammonia production from the combined reformer and methanol section effluent is 60854 kg/h.

The invention claimed is:

1. A process for co-production of ammonia and methanol comprising the following sequence of operations:

desulfurization of a hydrocarbon feed gas in the presence of hydrogen in a desulfurization unit, addition of steam to the desulfurized natural gas followed by reforming in a reformer, shift in a shift section comprising a high temperature shift part and a low temperature shift part, carbon dioxide removal and methanation, wherein the outlet stream from the reformer is split into two parts, one of which is subjected to shift, carbon dioxide removal, methanation, compression and ammonia synthesis, while the other part is compressed and fed to a once-through methanol synthesis section, methanol is withdrawn from the methanol synthesis section, and the remaining effluent from said section is divided into two streams comprising hydrogen, one of the two streams comprising hydrogen is fed to the shift section, and the other stream comprising hydrogen is recycled to the desulfurization unit.

2. The process according to claim 1, wherein the methanol synthesis section comprises one methanol synthesis reactor or two or three such reactors connected in series.

3. The process according to claim 1, wherein the part of the reformer outlet stream, which is compressed and fed to the methanol synthesis section, is compressed to 40-100 bars.

4. The process according to claim 3, wherein the part of the reformer outlet stream, which is compressed and fed to the methanol synthesis section, is compressed to around 80 bars.

5. The process according to claim 1, wherein the stream comprising hydrogen, which is transferred to the shift section, is directed to a point between the high temperature shift part and the low temperature shift part.

* * * * *